United States Patent [19]
Chin

[11] Patent Number: 5,976,142
[45] Date of Patent: Nov. 2, 1999

[54] APPARATUS AND METHOD FOR DISTRACTION OSTEOGENESIS OF SMALL ALVEOLAR BONE

[76] Inventor: Martin Chin, 20 Hampton Ct., Alameda, Calif. 94502

[21] Appl. No.: 09/026,600

[22] Filed: Feb. 20, 1998

Related U.S. Application Data

[63] Continuation-in-part of application No. 08/732,064, Oct. 16, 1996, Pat. No. 5,769,850.

[51] Int. Cl.$^6$ .................................................. A61B 17/86
[52] U.S. Cl. ............................................... 606/73; 606/96
[58] Field of Search ................................. 606/53, 60, 69, 606/70, 71, 72, 73, 76, 105; 433/173–176

[56] References Cited

U.S. PATENT DOCUMENTS

| | | | |
|---|---|---|---|
| 3,971,134 | 7/1976 | Bokros | 32/10 |
| 4,225,668 | 9/1980 | Bartoli | 433/176 |
| 4,439,152 | 3/1984 | Small | 433/173 |
| 4,522,596 | 6/1985 | Ashkinazy | 433/173 |
| 4,573,917 | 3/1986 | Erickson | 433/75 |

(List continued on next page.)

FOREIGN PATENT DOCUMENTS

| | | | |
|---|---|---|---|
| WO 96/19946 | 7/1996 | WIPO . | |
| WO 96/22061 | 7/1996 | WIPO | A61C 8/00 |

OTHER PUBLICATIONS

"Le Fort III Acvancement With Gradual Distraction Using Internal Devices", Authors: Martin Chin, D.D.S., and Bryant A. Toth, M.D., Plastic and Reconstructive Surgery, Sep., 1997, vol. 100, No. 4.

Akizuki, T., et al., "*Mid–face Distraction*," Craniofacial Surgery–Proceedings of the Sixth International Congress of The International Society of Cranio–Facial Surgery, Saint–Tropez 1995.

Chin, M., et al., "*Distraction Osteogenesis in Craniofacial Surgery Using Internal Devices*," Craniofacial Surgery–Proceedings of the Sixth International Congress of The International Society of Cranio–Facial Surgery, Saint–Tropez 1995.

Chin, Martin, DDS, et al. "Distraction Osteogenesis in Maxillofacial Surgery Using Internal Devices: Review of Five Cases," Journal of Oral and Maxillofacial Surgeons, vol. 54, pp. 45–53, 1996.

Costantino, Maj Peter D., MC, USAF; et al., "Experimental Mandibular Regrowth by Distraction Osteogenesis—Long–term Results," Arch Otolaryngol Head Neck Surg—vol. 119, May 1993.

Diner, P.A., et al., "*Intraoral Distraction for Mandibular Lengthening*," Craniofacial Surgery–Proceedings of the Sixth International Congress of The International Society of Cranio–Facial Surgery, Saint–Tropez 1995.

(List continued on next page.)

*Primary Examiner*—Michael Buiz
*Assistant Examiner*—David O. Reip
*Attorney, Agent, or Firm*—Fliesler, Dubb, Meyer & Lovejoy LLP

[57] ABSTRACT

An apparatus and method for osteogenesis distraction of small alveolar bone is provided. The alveolar distraction osteogenesis device may be affixed to small and thin bone segments. An alveolar distraction osteogenesis device according to the first embodiment includes a submergible first and second members along with a threaded rod. An alveolar distraction osteogenesis device according to a second embodiment includes an osseointegrated cylindrical member along with an adaptable threaded rod which may be used with a stabilizing plate. The alveolar distraction osteogenesis device is activated using a hexagonal drive wrench or a slot screw driver. In order to allow for bone growth and/or distraction, a constant activation rate between bone segments is applied by a torque.

12 Claims, 15 Drawing Sheets

U.S. PATENT DOCUMENTS

| | | | |
|---|---|---|---|
| 4,615,338 | 10/1986 | Hlizarov et al. | 128/92 A |
| 4,616,633 | 10/1986 | Vargas Garcia | 128/20 |
| 4,616,634 | 10/1986 | Vargas Garcia | 128/20 |
| 4,740,209 | 4/1988 | Gersdorff | 623/10 |
| 4,778,471 | 10/1988 | Bajpai | 623/16 |
| 4,813,869 | 3/1989 | Gatewood et al. | 433/18 |
| 4,872,840 | 10/1989 | Bori | 433/173 |
| 4,890,631 | 1/1990 | Hardy | 606/59 |
| 4,988,358 | 1/1991 | Eppley et al. | 623/16 |
| 5,006,070 | 4/1991 | Komatsu | 433/176 |
| 5,020,536 | 6/1991 | Keen | 128/402 |
| 5,052,930 | 10/1991 | Lodde et al. | 433/173 |
| 5,064,425 | 11/1991 | Brånemark et al. | 606/72 |
| 5,092,883 | 3/1992 | Eppley et al. | 623/11 |
| 5,205,746 | 4/1993 | Chanavaz | 433/174 |
| 5,211,664 | 5/1993 | Tepic et al. | 623/16 |
| 5,218,035 | 6/1993 | Liu | 524/414 |
| 5,224,958 | 7/1993 | Warunek et al. | 623/11 |
| 5,254,005 | 10/1993 | Zuest | 433/173 |
| 5,262,166 | 11/1993 | Liu et al. | 424/423 |
| 5,263,980 | 11/1993 | Leibinger et al. | 606/60 |
| 5,275,598 | 1/1994 | Cook | 606/54 |
| 5,281,265 | 1/1994 | Liu | 106/35 |
| 5,297,963 | 3/1994 | Dafatry | 433/172 |
| 5,302,127 | 4/1994 | Crisio, Jr. | 433/173 |
| 5,350,382 | 9/1994 | Armstrong | 606/87 |
| 5,361,506 | 11/1994 | Beeuwkes, III | 33/512 |
| 5,364,396 | 11/1994 | Robinson et al. | 606/53 |
| 5,380,328 | 1/1995 | Morgan | 606/70 |
| 5,389,323 | 2/1995 | Cook | 264/136 |
| 5,419,700 | 5/1995 | Sillard | 433/172 |
| 5,419,701 | 5/1995 | Propper | 433/173 |
| 5,427,527 | 6/1995 | Niznick et al. | 433/174 |
| 5,437,668 | 8/1995 | Aronson et al. | 606/57 |
| 5,449,291 | 9/1995 | Lueschen et al. | 433/173 |
| 5,456,601 | 10/1995 | Sendax | 433/173 |
| 5,474,063 | 12/1995 | Riendeau | 128/207.18 |
| 5,489,210 | 2/1996 | Hanosh | 433/173 |
| 5,496,256 | 3/1996 | Bock et al. | 601/2 |
| 5,513,989 | 5/1996 | Crisio | 433/176 |
| 5,538,427 | 7/1996 | Hoffman et al. | 433/173 |
| 5,542,847 | 8/1996 | Margulies | 433/173 |
| 5,564,922 | 10/1996 | Rosa et al. | 433/173 |
| 5,591,029 | 1/1997 | Zuest | 433/173 |
| 5,611,688 | 3/1997 | Hanosh | 433/174 |
| 5,681,167 | 10/1997 | Lazarof | 433/174 |
| 5,685,714 | 11/1997 | Beaty et al. | 433/172 |
| 5,695,336 | 12/1997 | Lazzara et al. | 433/173 |
| 5,697,779 | 12/1997 | Sachdeva et al. | 433/2 |

OTHER PUBLICATIONS

Fairley, J., et al., "*Continuous Midfacial Distraction*," Craniofacial Surgery–Proceedings of the Sixth International Congress of The International Society of Cranio–Facial Surgery, Saint–Tropez 1995.

Guerrero, R., et al., "*Craniofacial Osteogenesis by Gradual Distraction*," Craniofacial Surgery–Porceedings of the Sixth International Congress of The International Society of Cranio–Facial Surgery, Saint–Tropez 1995.

McCormick, Suzanne, DDS, "Distraction Osteogenesis," Dentistry Today, Sep. 1996, p. 58.

Monasterio, F. O., et al., "*Simultaneous Mandibular and Maxillary Distraction*," Craniofacial Surgery–Proceedings of the Sixth International Congress of The International Society of Cranio–Facial Surgery, Saint–Tropez 1995.

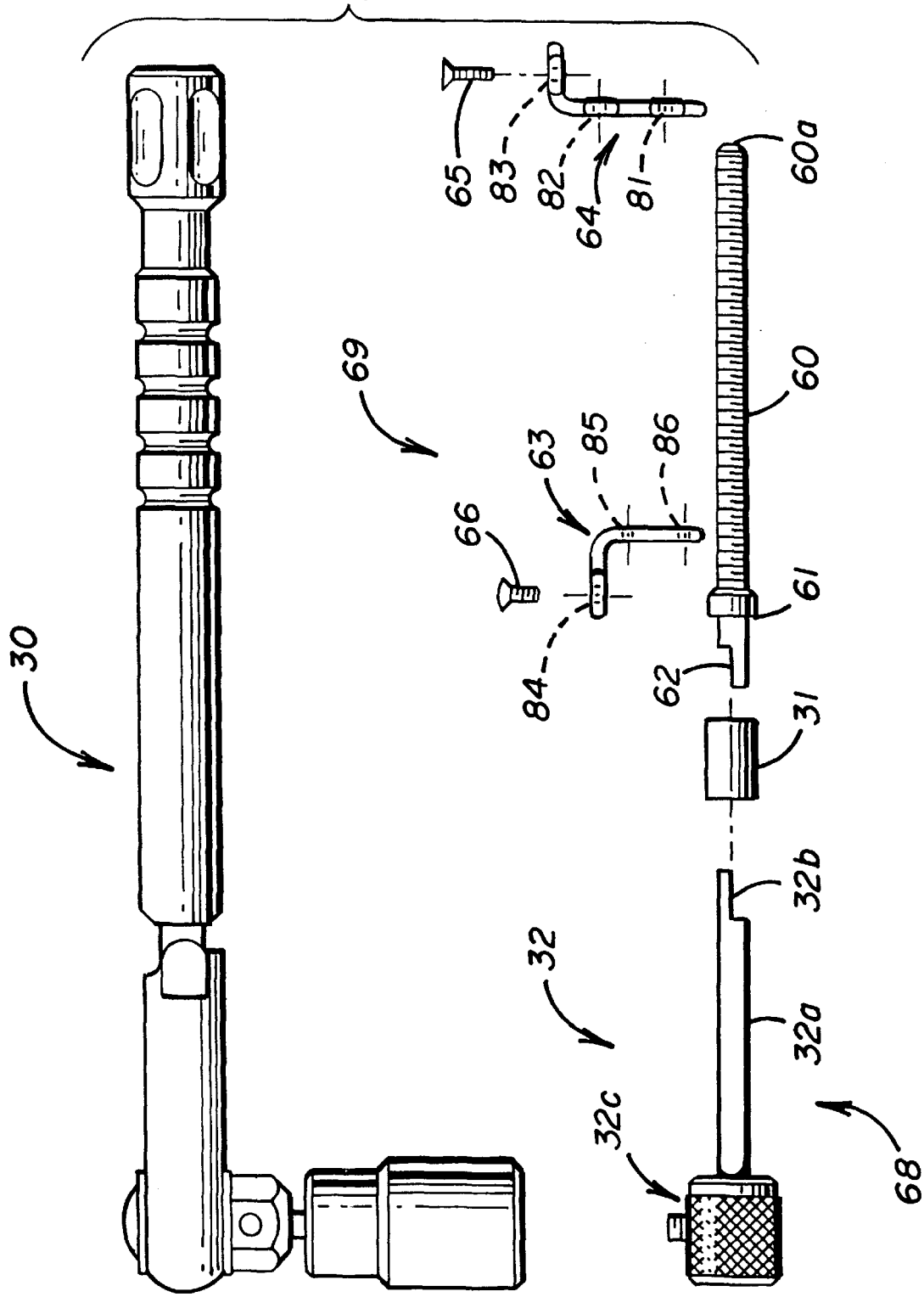

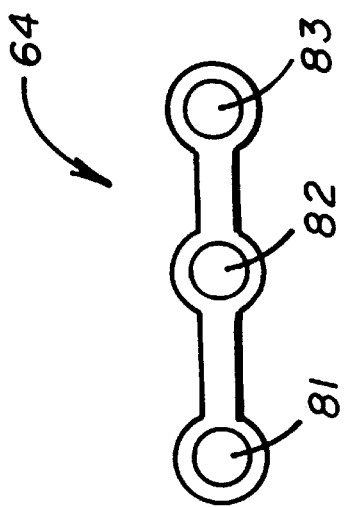
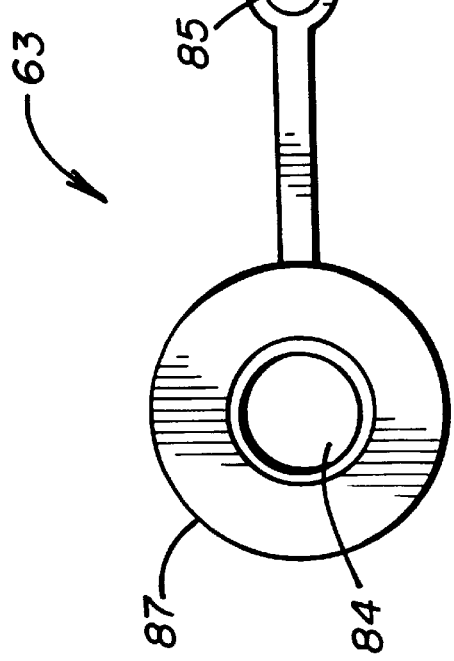
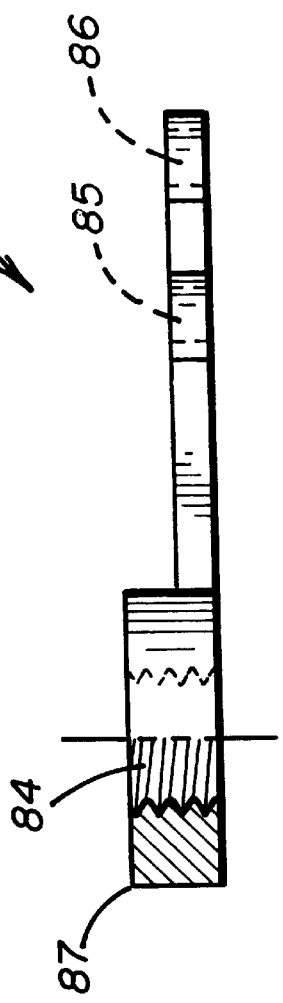

APPARATUS AND METHOD FOR DISTRACTION OSTEOGENESIS OF SMALL ALVEOLAR BONE

This application is a continuation-in-part of Ser. No. 08/732,064, filed on Oct. 16, 1996, now U.S. Pat. No. 5,769,850.

BACKGROUND OF THE INVENTION

1. Field of the Invention

The present invention relates to distraction osteogenesis, and in particular, distraction osteogenesis of small alveolar bone.

CROSS-REFERENCE TO RELATED APPLICATIONS

The following U.S. patents are assigned to the assignee of the present application, are related to the present application and their disclosures are incorporated herein by reference:

(A) U.S. patent application Ser. No. 08/732,064, filed on Oct. 16, 1996 by Martin Chin and entitled AN APPARATUS AND METHOD FOR SUBMERGIBLE, SELF-RETAINING DISTRACTION OSTEOGENESIS.

(B) U.S. Divisional Patent Application Ser. No. 09/006,143 filed on Jan. 13, 1998 by Martin Chin and entitled AN APPARATUS AND METHOD FOR SUBMERGIBLE, SELF-RETAINING ZYGOMA DISTRACTOR which is a divisional of U.S. patent application Ser. No. 08/732,064.

2. Description of the Related Art

Distraction osteogenesis refers to a technique for growing bone or osteogenesis material, as well as soft tissue, by separating two bone segments. Generally, an osteotomy, such as a Lefort III osteotomy, is performed which partitions a bone into two bone segments. External distraction osteogenesis devices are then attached to the bone segments through soft tissue or a skin layer. These external distraction osteogenesis devices may include rods and rings or other cumbersome metal components. The distraction osteogenesis devices form a gap between the bone segments by exerting pressure between the bone segments. As the gap between the bone segments widens, the body's own natural healing capacity fills the void with new bone and adjacent soft tissue. Once the desired bone formation is achieved, the area is allowed to heal and consolidate. Often, the distraction osteogenesis device is then removed.

An example of a distraction osteogenesis device is an Ilizarov distractor. Typically, an Ilizarov distractor is used in lengthening individuals' limbs, such as a leg. In this application, an Ilizarov distractor may include external metal rings which are then secured to two bone segments in a leg. These metal rings are then attached by a rod assembly which may be used to form a gap between the two bone segments and thus allow for the formation of new bone. A description of an Ilizarov distractor may be found in U.S. Pat. No. 4,615,338, issued to Ilizarov, et al. on Oct. 7, 1986 and entitled "Automatic Compression—Distraction Apparatus."

Distraction osteogenesis devices may also be used in growing bone in the craniofacial region of small children. Often, distraction osteogenesis devices are used on small children who are missing bone due to birth abnormalities or accidents. While distraction osteogenesis devices are often used on children, distraction osteogenesis devices may be used on adults and animals as well.

A number of problems are encountered in using present distraction osteogenesis devices. First, distraction osteogenesis devices are generally external, which may cause a number of problems or complications. Often, cumbersome metal rods and rings located external to an individual's skin are used to distract or separate bone segments. Individuals, and in particular small children, may fall and injure themselves on the protruding metal edges. Further, small children may complicate the distraction osteogenesis procedure by improperly adjusting the osteogenesis distraction device.

The distraction osteogenesis device may require multiple entry points to an individual's skin and thus may create multiple scars. Distraction osteogenesis devices requiring multiple entry points may also increase the likelihood of infection due to the multiple openings in the individual's skin. Also, individuals undergoing the distraction osteogenesis procedure have to cope with an external device which is not cosmetically appealing.

A second problem encountered with distraction osteogenesis devices regards customizing devices for individuals. Generally, a distraction osteogenesis device used for one individual would not be suitable for another. In distraction osteogenesis devices used in the craniofacial area, distraction osteogenesis devices must be measured to fit specific surface areas of craniofacial bones. Also, individuals may have different amounts of bone caused by different types of birth abnormalities or accidents, thus requiring customized distraction osteogenesis devices due to limited bone.

Third, distraction osteogenesis devices are attached to bone segments in such a way that the point of fixation to the bone transfers force during activation. For example, a distraction osteogenesis device may be attached to a bone segment by a bone screw or rod which transfers a substantial amount of force during activation or when the distraction osteogenesis device is exerting pressure between the bone segments. By having the bone screw transfer a substantial amount of the force during activation, the distraction osteogenesis device may be dislodged from the bone.

Fourth, distraction osteogenesis devices are activated using constant rates which do not reflect the individual's healing abilities. Regardless of the age or condition of the individual, distraction osteogenesis devices are activated by widening the gap between bone segments 0.25–0.50 mm four times per day. This conventional activation rate results in bone growth as low as 20 mm in 20 days. Accordingly, an individual may have to be under constant medical supervision for up to 20 days. An individual could be an outpatient, but would need to return to the hospital four times per day for adjustments. Present distraction osteogenesis device activation techniques do not take into account an individual's ability to grow bone at a greater or lesser rate. By using this constant rate, bone may grow too quickly and lock the distraction osteogenesis device, or in the alternative, bone may grow too slowly, requiring a longer period of time that the distraction osteogenesis device is necessary.

Fifth, distraction osteogenesis devices are often difficult to attach because limited bone is available. There may be different amounts of bone caused by different types of birth abnormalities or accidents. Further, microsurgical reconstruction may be desired. For example, a distraction osteogenesis device may be necessary for a dental implant surgery on a bone graft not large enough to place a dental implant. Thus, small alveolar bone distraction osteogenesis devices are required to accommodate bone and space limitations.

Therefore, it is desirable to provide a distraction osteogenesis device which is submergible, or beneath an individual's skin or soft tissue. The distraction osteogenesis device then could be permanently positioned within an individual, thereby eliminating the need for surgery in removing the device, including the associated risks and costs. The distraction osteogenesis device then would be more cosmetically appealing and reduce the likelihood of infection, injury and/or scaring. Further, it is desirable to have a distraction osteogenesis device which does not have to be customized for each individual. Manufacturing and medical costs would then be substantially reduced by using a standard distraction osteogenesis device and method, rather than customizing distraction osteogenesis devices and methods for each individual. The distraction osteogenesis device also should be affixed to bone in such a way that a substantial amount of the force used in activation is not transferred through a fastening device (i.e., screw, pin or rod). Moreover, the distraction osteogenesis device should be activated at a rate which optimizes bone growth. Finally, it is desirable to provide a distraction osteogenesis device which may be affixed to small and thin bone segments. The distraction osteogenesis device could then be utilized in more surgical procedures.

SUMMARY OF THE INVENTION

According to an aspect of the present invention, an apparatus is provided for distracting a first bone segment from a second bone segment. The apparatus comprises a first implantable member for coupling the first bone segment and a second implantable member for coupling the second bone segment. Submergible means is coupled to the first member and the second member which positions the first member a distance from the second member responsive to a force.

According to another aspect of the present invention, the submergible means includes a threaded rod portion.

According to another aspect of the present invention, the apparatus includes activating means for transferring a force to the submergible means.

According to another aspect of the present invention, the activating means includes a cannula, a torque wrench adapter and a torque wrench.

According to another aspect of the present invention, the apparatus includes means for removing the activating means.

According to another aspect of the present invention, the first and second members transfer a substantial amount of the force.

According to another aspect of the present invention, the activating means transfers a force generating a maximum pressure in order to achieve a maximum distance.

According to another aspect of the present invention, a submergible device for distracting a first segment of alveolus from a second segment of alveolus to allow for bone generation is provided. The submergible device comprises a rod having a threaded portion, including an end, a base and an activation end. A first member is coupled to the first segment of alveolus and has an opening for inserting the rod end. A second member is coupled to the second segment of alveolus and has an opening for positioning the threaded portion of the rod. The rod transfers a force against the second member, creating a distance between the first and second alveolus segments.

According to another aspect of the present invention, a method for forming alveolar bone is provided. The method includes the steps of: (a) cutting the alveolus into first and second segments; (b) securing a first plate to the first segment of alveolus; (c) forming an opening in the second segment of alveolus; (d) securing a second transport plate to the second segment of alveolus; (e) inserting a rod into the opening of the second segment of alveolus and through the second plate opening to the first plate; and (f) exerting a force on the rod to displace the first segment of alveolus from the second segment of alveolus.

According to another aspect of the present invention, a small alveolar bone device for distracting a first segment of alveolus from a second segment of alveolus to allow for bone generation is provided. The device comprises a cylindrical member having a threaded inner surface coupled to the first segment of alveolus. A rod adapter having a threaded outer surface and a threaded inner surface mates to the threaded inner surface of the cylindrical member. A rod having a threaded outer surface mates to the threaded inner surface of the rod adapter. The rod transfers a force against the second segment of alveolus, creating a distance between the first and second alveolus segments.

According to another aspect of the present invention, a method for forming small alveolar bone is provided. The method includes the steps of: (a) forming an opening in the alveolus; (b) inserting the cylindrical member into the opening in the alveolus; (c) inserting an obturating member in the cylindrical member to prevent bone and tissue from growing into the cylindrical member while the alveolus grows into substantially intimate contact with the cylindrical member; (d) removing the obturating member; (e) inserting a drill guide member in the cylindrical member; (f) forming a second opening in the alveolus with a drill guided by the drill guide member; (g) removing the drill guide member; (h) cutting the alveolus into a first bone segment and a second bone segment, the first bone segment containing the cylindrical member and the second opening; (i) inserting a rod adapter into the cylindrical member; (j) inserting a rod into the opening of the alveolus and through the rod adapter to the second bone segment; and, (k) exerting a force on the rod in order to displace the first bone segment from the second bone segment.

Other aspects and advantages of the present invention can be seen upon review of the figures, the detailed description, and the claims which follow.

BRIEF DESCRIPTION OF THE DRAWINGS

FIG. 1 illustrates an alveolar distraction osteogenesis apparatus, including an alveolar distraction device, cannula, torque wrench adapter and torque wrench according to the present invention.

FIGS. 3a–c illustrate alveolar distraction osteogenesis plates according to the present invention.

DETAILED DESCRIPTION OF THE INVENTION

I. Alveolar Distraction Osteogenesis Apparatuses

Figure 2A:
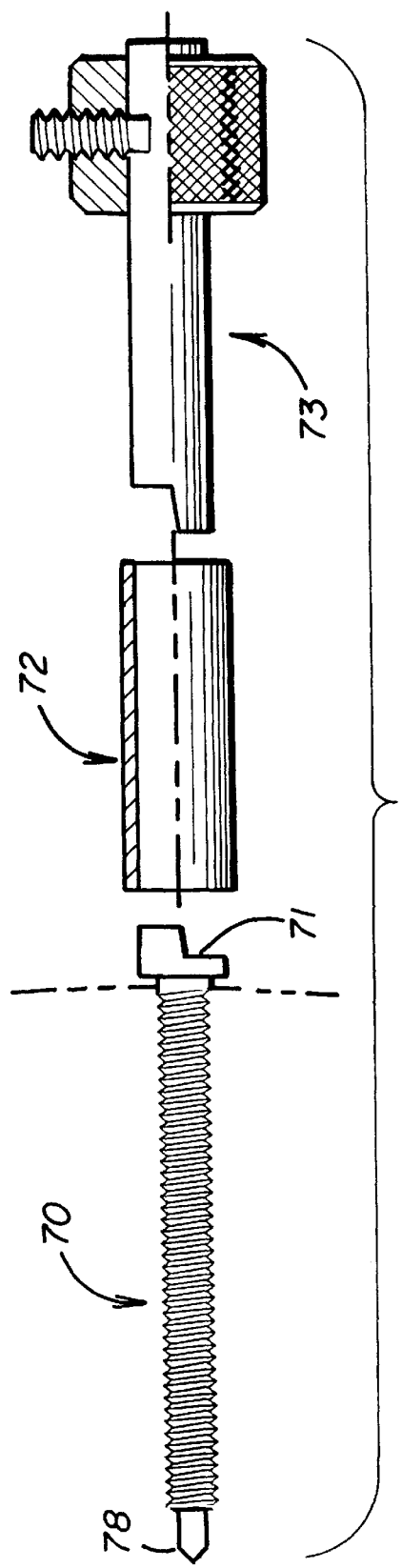
FIGS. 2a–b illustrate an alveolar distraction osteogenesis rod, cannula and torque wrench adapter according to the present invention.

FIG. 1 illustrates alveolar distraction osteogenesis apparatus 68. The alveolar distraction osteogenesis apparatus 68 is used to form bone in the alveolus which may be missing due to an accident or birth abnormality. Often, alveolus must be formed in order for dental implants to be used. The alveolar distraction osteogenesis apparatus 68 includes a torque wrench 30, adapter 32 and cannula 31.

The alveolar distraction osteogenesis apparatus 68 also includes an alveolar distraction osteogenesis device 69. The alveolar distraction osteogenesis device 69 includes a rod 60 having base 61, activation end 62 and end 60a. The alveolar distraction osteogenesis device 69 also includes a transport bone segment plate 63 and stabilizing plate 64. Plates 63 and 64 may be secured by screws 66 and 65, respectively.

Figure 2B:
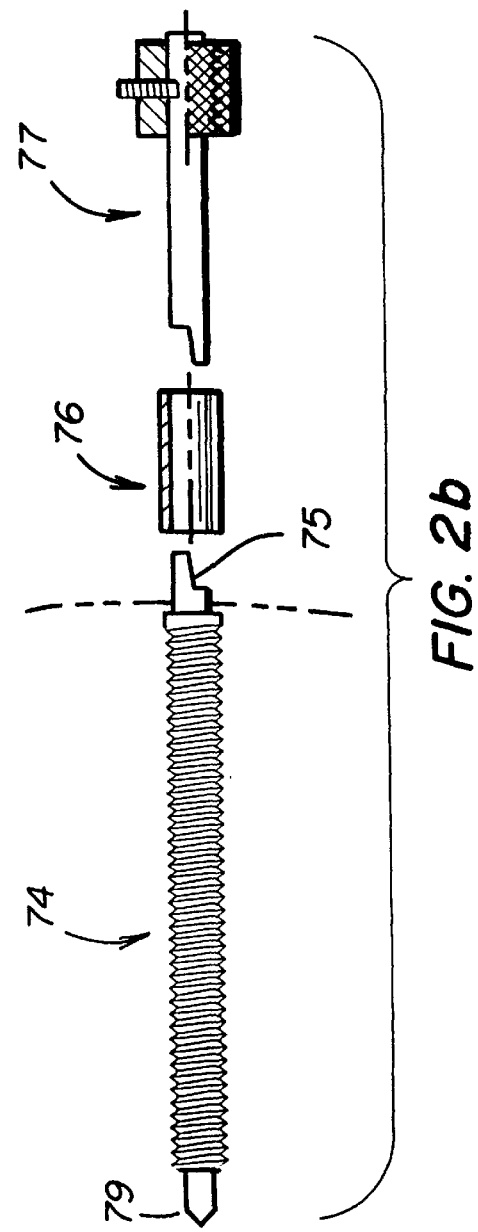

FIGS. 2a–b illustrate two embodiments of an alveolar distraction osteogenesis device 69 shown in FIG. 1. FIG. 2a illustrates a nonsubmergible alveolar distraction osteogenesis device, while FIG. 2b illustrates a submergible alveolar distraction osteogenesis device. The nonsubmergible alveolar distraction osteogenesis device in FIG. 2a includes rod 70, cannula 72 and adapter 73. Rod 70 includes base 71 and end 78. The submergible alveolar distraction osteogenesis device shown in FIG. 2b includes rod 74, cannula 76 and adapter 77. Rod 74 includes base 75 and end 79. The nonsubmergible alveolar distraction osteogenesis device illustrated in FIG. 2a has a rod 70 with a base 71 which may be positioned substantially above soft tissue and/or a skin layer, while base 75 of rod 74 is positioned below soft tissue and/or a skin layer. Finally, the alveolar distraction osteogenesis device illustrated in FIG. 2b has a diameter of approximately 1.6 mm and a pitch of 0.35 mm per revolution, while the alveolar distraction osteogenesis device illustrated in FIG. 2a has a diameter of approximately 2.0 mm and a pitch of 0.4 mm per revolution.

FIGS. 3a–c illustrate the transport bone segment plate 63 and stabilizing plate 64 illustrated in FIG. 1. In an embodiment, stabilizing plate 64 consists of a titanium member having openings 81, 82 and 83. In an embodiment, a greater or lesser amount of openings may be used. Openings 82 and 83 are used to fix plate 64 to bone with inserted screws. Further, embodiments may not require plate 64 if the bone material is sufficiently hard. The titanium member may be bent approximately 90° between openings 81 and 82, as seen in plate 64 of FIG. 1, to fit the alveolus. In an embodiment, opening 83 is an approximately 1 mm opening for positioning a rod, such as rod end 79 shown in FIG. 2b.

In an embodiment, transport bone segment plate 63 also is a titanium member having three openings 84, 85 and 86, as illustrated in FIGS. 3b–c. In an embodiment, a greater or lesser amount of openings may be used. Openings 85 and 86 are used to fix transport bone segment plate 63 to bone with inserted screws. In an embodiment, both plates 64 and 63 are available from Pfizer Pharmaceuticals, Inc., located at Valley Lab, Inc., P.O. Box 9015, 5920 Longbow Drive, Boulder, Colo. 80301-9015. The screws, such as screws 66 and 65, as shown in FIG. 1, are also available from Pfizer Pharmaceuticals, Inc. In an embodiment, the diameter of washer-shaped member 87 surrounding opening 84 is approximately 0.175 inches, while openings at 85 and 86 are approximately 1.0 mm. In an embodiment, the width of the washer-shaped member 87 is approximately 5 mm. The threaded portion of opening 84 has a diameter of approximately 2 mm and a pitch of 0.4 mm per revolution for rod 70 and approximately 1.6 mm and a pitch of 0.35 mm per revolution for rod 74. Threaded opening 84 is used to position rod 60. As with plate 64, transport bone segment plate 63 may be bent approximately 90° between openings 85 and 84, as seen in transport bone segment plate 63 of FIG. 1, to fit the alveolus.

In an embodiment, a computed tomography scan of the area for distraction osteogenesis may be obtained. Alveolar distraction osteogenesis device 69 may then be manufactured using the information from computed tomography. For example, the length of rod 60 may be determined from this imaging information. Moreover, the amount of bone available and/or number of screws used to affix the alveolar distraction osteogenesis device, may be estimated based upon the image information. In the preferred embodiment, a customized alveolar distraction osteogenesis device is not used and alveolar distraction osteogenesis device 69 having the above-described configuration and size suitable for a majority of individuals is used.

The alveolar distraction osteogenesis device may be implanted, and is thus submergible, beneath a layer of soft tissue. Thus, the alveolar distraction osteogenesis device is less likely to scar and is more cosmetically appealing and comfortable than external distraction osteogenesis devices. A submerged alveolar distraction osteogenesis device is less likely to become infected than external devices. Also, the fixation points, in particular screws, which fix the plates to bone do not transfer a substantial amount of force during activation. The screws are used to fix the plates and are inserted substantially perpendicular to the pressure separating the bone segments. The alveolar distraction osteogenesis device may also be activated using a maximum pressure, rather than at conventional constant activation rates, as will be described.

Figure 7:
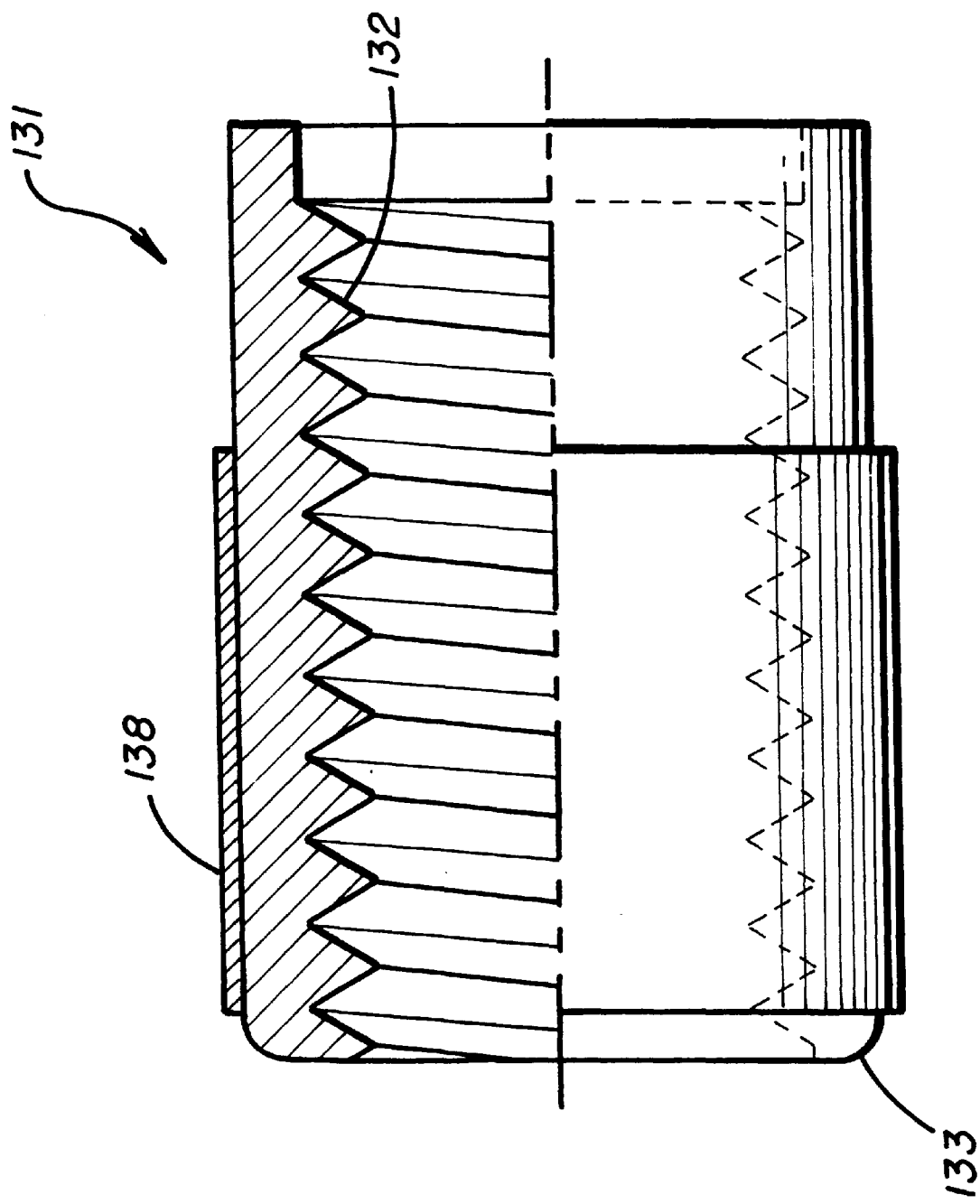
FIG. 7 illustrates an alveolar distraction osseointegrated cylindrical member according to another embodiment of the present invention.

FIGS. 7–11 illustrate an alveolar distraction osteogenesis apparatus according to another embodiment which is preferably used with small and thin bone segments. FIG. 7 illustrates the osseointegrated transport cylindrical member 131. The transport cylindrical member 131 is a titanium member having a cylindrical body with an internal opening 132 and a curved end 133. Internal opening 132 is threaded and used to couple threaded portion of rod 60 via an adapter during the distraction. In an embodiment, the outside diameter of the transport cylindrical member 131 is approximately 3.3 mm and the length is approximately 0.20 in. The threaded portion of the opening 132 has a diameter of approximately 3 mm and a pitch of 0.5 mm. The transport cylindrical member 131 is covered with a coating 138 of bondable titanium plasma or hydroxlyappatite which enhances the osseointegration process. In an embodiment, cylindrical member 131 is modified from a dental implant part available from Steri-Oss located at 22895 Eastpark Drive, Yorba Linda, Calif., 92887. The threads on the internal opening are machined down to 3.0 mm. The length of the part is shortened to 0.20 in. The bottom of the part is removed by drilling so that a cylinder is formed, and an internal machined taper is removed from the top of the part.

Figure 8:
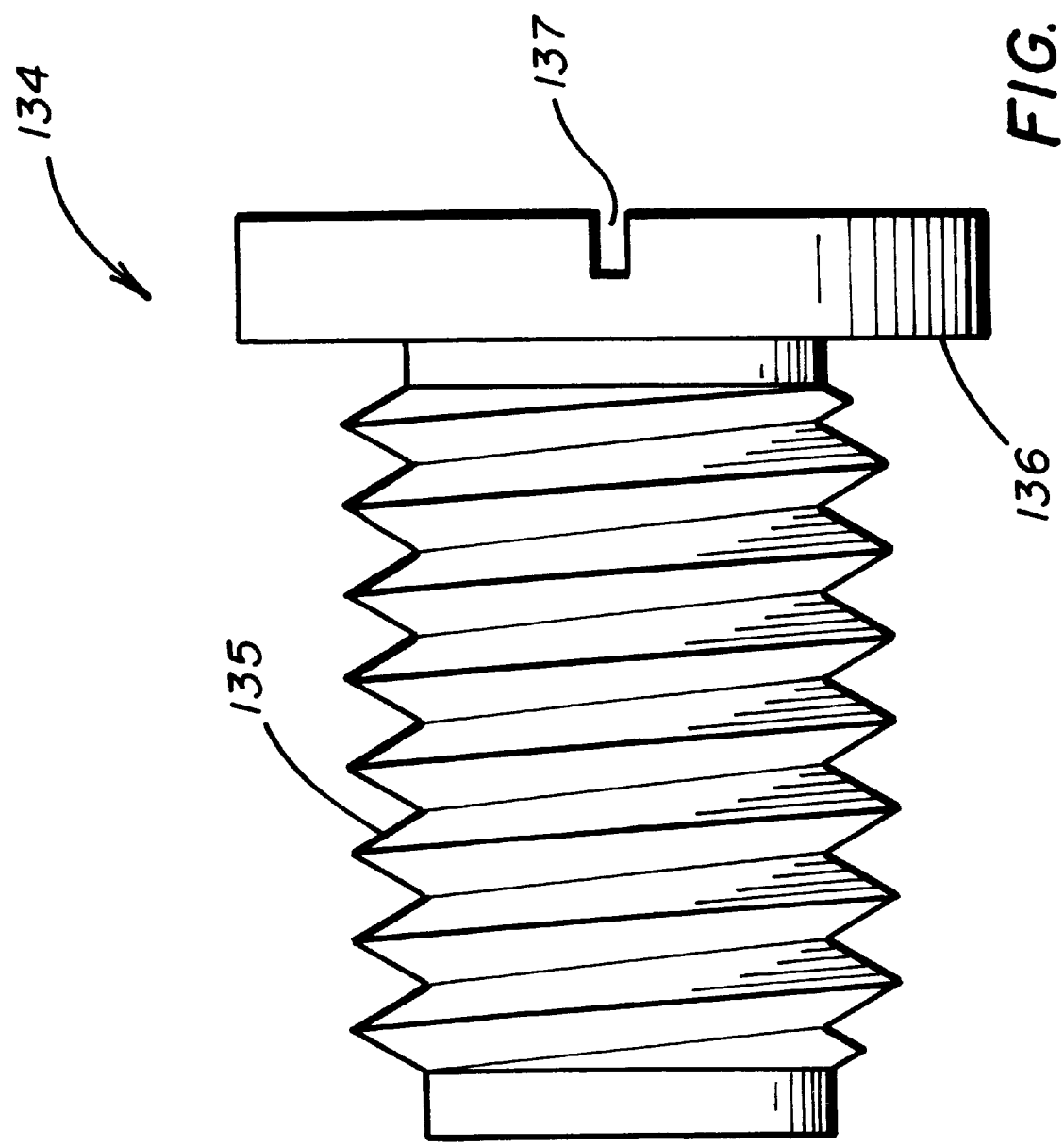
FIG. 8 illustrates an alveolar distraction obturating screw according to another embodiment of the present invention.

FIG. 8 illustrates an obturating screw 134 which is a titanium member having a threaded portion 135 and a circular top 136 having a slot 137. The obturating screw 134 and top 136 are inserted into the internal opening 132 of the transport cylindrical member 131 by a slotted screw driver engaged in slot 137. The obturating screw 134 prevents growing bone and tissue from growing into the internal opening 132 during the healing phase of osseointegration. The threaded portion of obturating screw 134 has a diameter of approximately 3 mm and a pitch of 0.5 mm. The top 136 has a diameter of approximately 3.3 mm and the total length of obturating screw 134 is approximately 0.20 in. In an embodiment, the obturating screw 134 is modified from a dental implant part available from SteriOss located at 22895 Eastpark Drive, Yorba Linda, Calif., 92887. The diameter of the top of the part is machined down from 4.0 mm to 3.3 mm.

Figure 9:
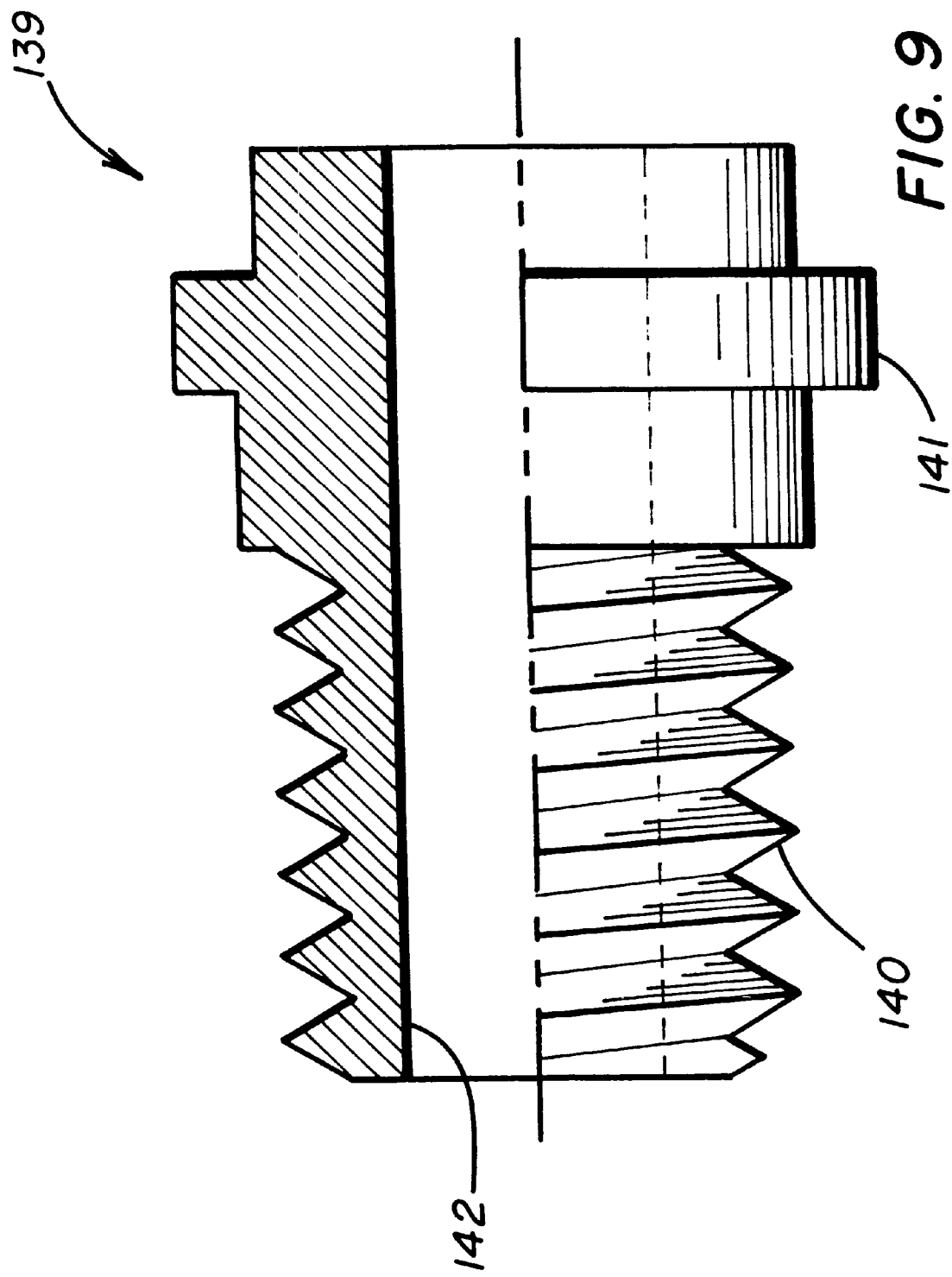
FIG. 9 illustrates an alveolar distraction drill guide according to another embodiment of the present invention.

FIG. 9 illustrates a drill guide 139 which is a titanium member having a threaded portion 140, a circular top 141 and an internal opening 142. The drill guide 139 is inserted into the internal opening 132 of the transport cylindrical member 131 and used as protection for the threads in the internal opening 132 of the transport cylindrical member 131 during drilling of the alveolus segment. The threaded portion of the drill guide 139 has a diameter of approximately 3 mm, a pitch of 0.5 mm, and a length of approximately 0.1 inches. The circular top 141 has a diameter of approximately 3.3 mm. The total length of drill guide 139 is approximately 5.0 mm having an internal opening 142 with a diameter of approximately 2.05 mm. In an embodiment, drill guide 139 is modified from a dental implant part available from Attachments International located at 600 S. Amphlett Blvd., San Mateo, Calif., 94402. The diameter of the internal opening of the part is machined down from 1.6 mm to 2.05 mm.

Figure 10:
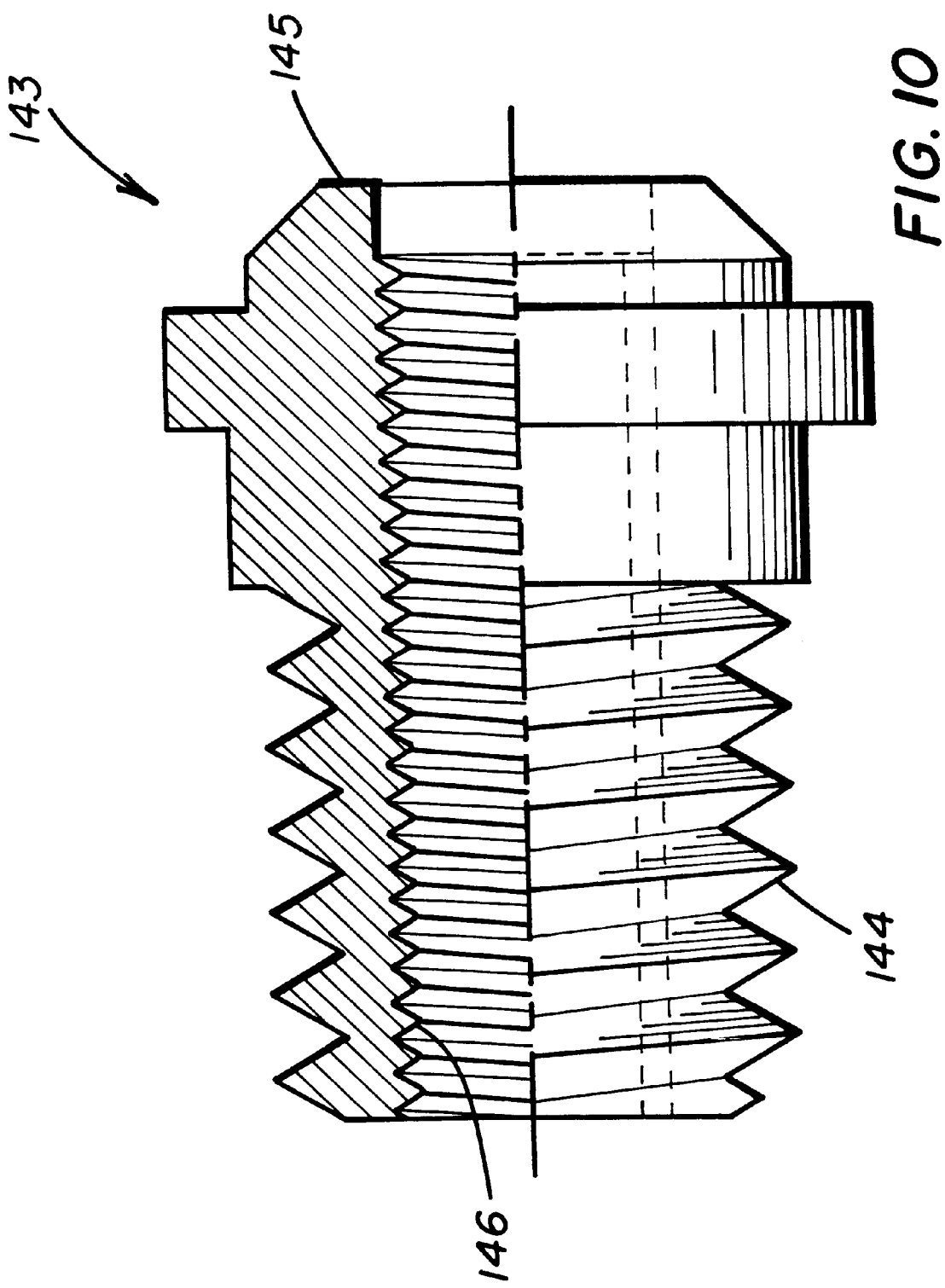
FIG. 10 illustrates an alveolar distraction rod adapter for use with a hexagonal drive wrench according to another embodiment of the present invention.

FIG. 10 illustrates a rod adapter 143 which is a titanium member having a threaded outer portion 144, a hexagonal top 145 and a threaded internal opening 146. The rod adapter 143 is inserted into the internal opening 132 of the transport cylindrical member 131 and reduces the internal opening diameter of the transport cylindrical member 131 so that rod 60 may be activated by a hexagonal drive wrench. In an embodiment, the rod adapter 143 is preferred in distraction procedures where insertion of the rod adapter may be difficult due to the position of the cylindrical member 131. The rod adapter 131 facilitates insertion because it is self-retaining with a self locking hexagonal drive wrench. The rod adapter 143 is also preferred when there is not limited space in the distraction procedure. The threaded outer portion 144 of the rod adapter 143 has a diameter of approximately 3 mm, a pitch of 0.5 mm, and a length of approximately 0.125 inches. The threaded internal opening 146 has a diameter of approximately 2 mm and a pitch of 0.4 mm. The hexagonal top 145 has a diameter of approximately 4.0 mm and the total length of rod adapter 143 is approximately 0.25 in. In an embodiment, rod adapter 143 is modified from a dental implant part available from Attachments International located at 600 S. Amphlett Blvd., San Mateo, Calif., 94402. The diameter of the threaded internal opening of the part is machined down from 1.6 mm to 2.0 mm. and the bottom of the part is removed by drilling so that a cylinder is formed.

Figure 11:
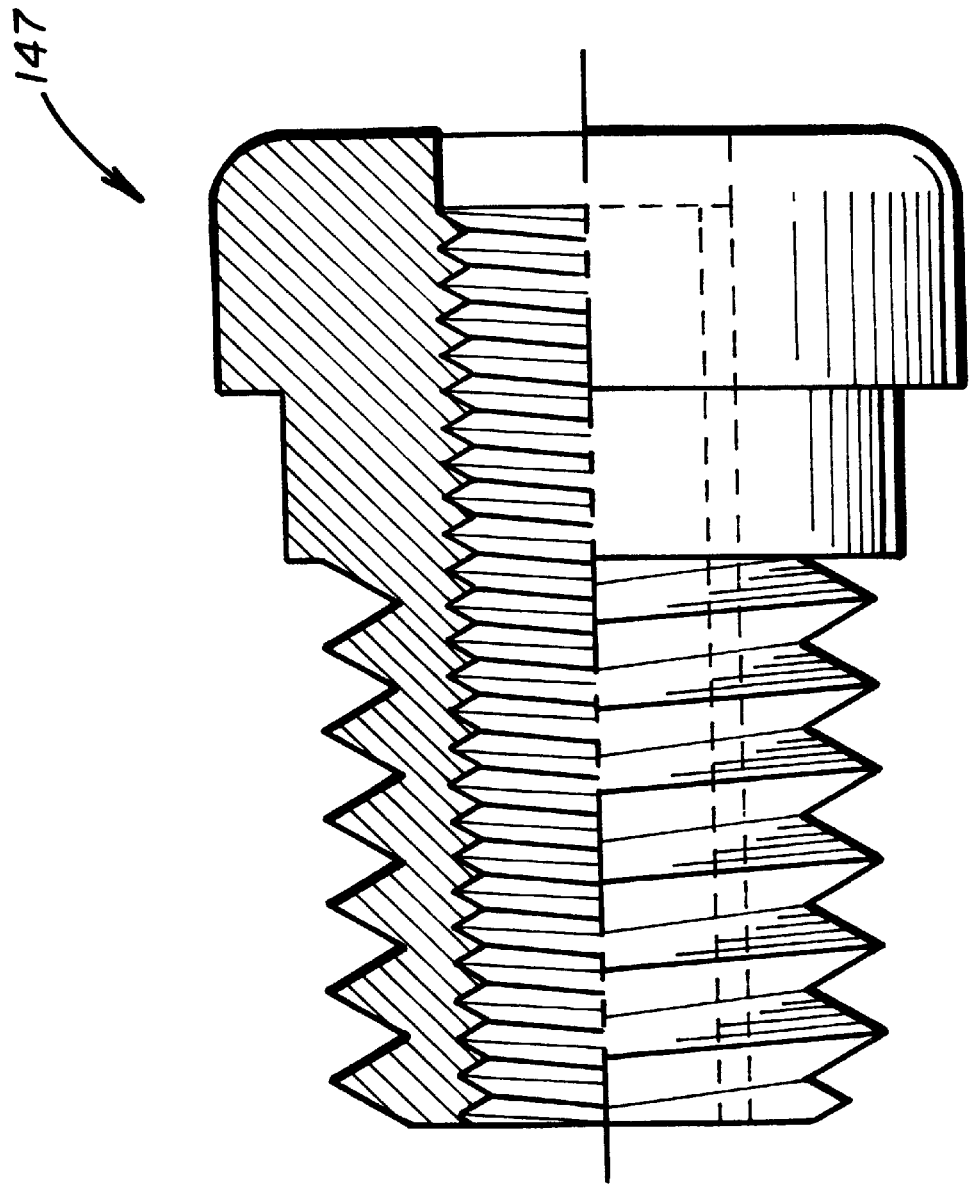
FIG. 11 illustrates an alveolar distraction rod adapter for use with a slot screw driver according to another embodiment of the present invention.

FIG. 11 illustrates another embodiment of a rod adapter 147 which is activated by a slot screw driver. The slot screw driver rod adapter 147 is similar to rod adapter 143 except hexagonal top 145 is removed. The hexagonal top 145 of rod adapter 143 occupies space that bone may be transported into during distraction. In an embodiment, rod adapter 147 allows for greater distraction because rod 60 may be inserted into the alveolar bone up to 3.0 mm further. Rod adapter 147 is preferred in limited spaces or when greater bone growth is desired. In an embodiment, rod adapter 147 is modified from a dental implant part in the same manner as rod adapter 143, and is available from Attachments International located at 600 S. Amphlett Blvd., San Mateo, Calif., 94402.

II. Alveolar Distraction Osteogenesis Device Inserting and Activating Methods

Figure 4A:
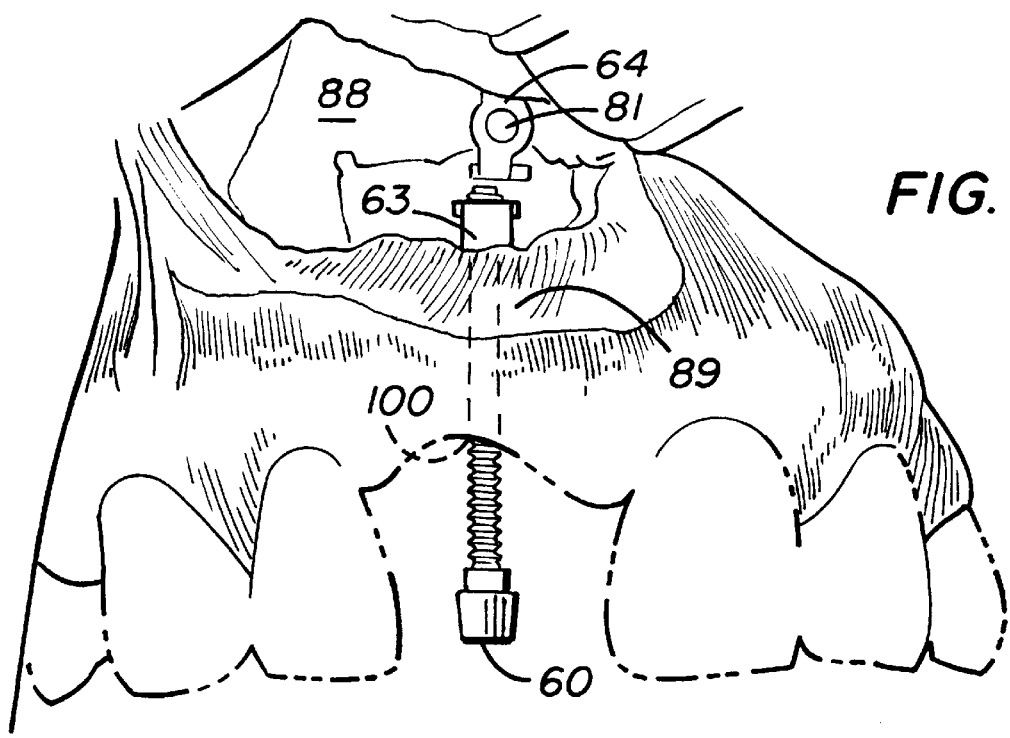
FIGS. 4a–b illustrate the steps of inserting an alveolar distraction osteogenesis device.
Figure 4B:
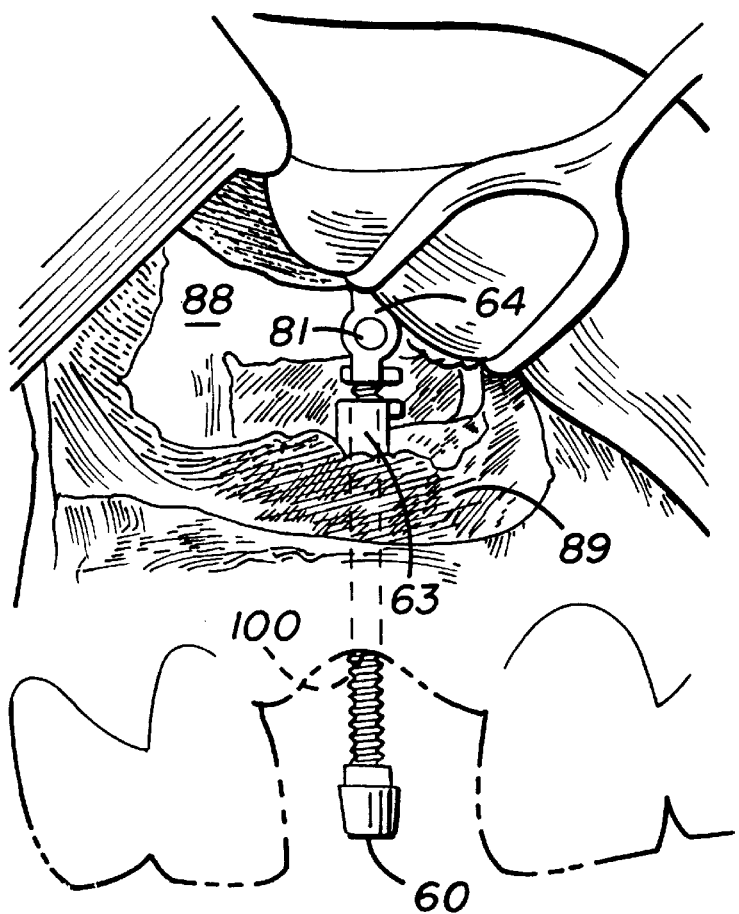

FIGS. 4a–b illustrate a surgical view of an osteotomy and an inserted alveolar distraction osteogenesis device according to the present invention. Specifically, FIGS. 4a–b illustrate a rod 60 inserted into stabilizing plate 64 and transport bone segment plate 63.

After determining the size of rod 60, an osteotomy is performed on the alveolus to form upper alveolus segment 88 and lower alveolus segment 89. An opening 100 is then drilled into the lower alveolus segment 89. In an embodiment, an approximately 2 mm wide opening is formed. Stabilizing plate 64 is then positioned on the upper alveolus segment 88, while bone transport segment plate 63 is positioned on the lower alveolus segment. Bone screws then may be positioned through openings 81, 82, 85 and 86 to fix the plates 63 and 64 to respective alveolus segments. FIGS. 4a–b illustrate a plate 64 without a screw in opening 81. Rod 60 is then inserted into opening 100 through lower alveolus segment 89 and through opening 84 of plate 63. Rod end 60a is then positioned in opening 83 of plate 64.

Figure 5A:
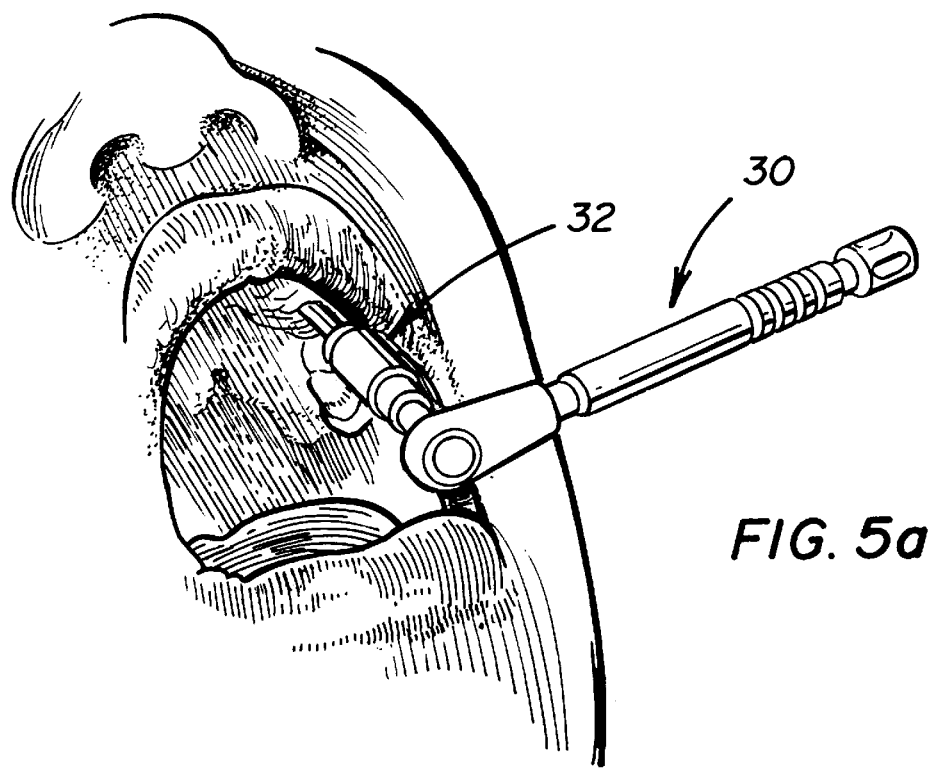
FIG. 5a illustrates activating an inserted alveolar distraction osteogenesis device.

The alveolar distraction osteogenesis device may be activated using a torque wrench 30 and adapter 32, as illustrated in FIG. 5a. Torque wrench 30, adapter 32 and cannula 31 are also illustrated in FIG. 1. Adapter 32 includes a rod 32a having a tapered bayonet end 32b for fitting rod activation end 62. Cannula 31 is first positioned over rod 60, in particular activation end 62. Adapter 32 is then used to couple rod 60 by inserting rod 32a into cannula 31. A hammer is then used to lodge the tapered end 32b of adapter 32 into activation end 62 of rod 60. Torque wrench 30 is then coupled to adapter interface 32c. In an embodiment, the torque wrench 30 may be available from Interpore International, 181 Technology Drive, Irvine, Calif. 92618.

A predetermined torque setting corresponding to a distraction pressure is then set on torque wrench 30. Torque wrench 30 is then rotated in order to create a force which separates plates 63 and 64 and thus upper alveolus segment 88 and lower alveolus segment 89. The torque wrench 30 setting corresponds to a pressure exerted by alveolar distraction osteogenesis device 69. The relationship between a torque wrench 30 setting and exerted alveolar distraction osteogenesis device 69 pressure is determined before inserting device 69. For example, it was discovered during clinical evaluations that a 14 Newton cm and 18 Newton cm torque wrench setting corresponds to 7 kg and 9 kg of pressure exerted by distraction osteogenesis device 69. In an embodiment, the amount of torque applied is based upon the maximum pressure the soft tissue can withstand without changing color, rather than using a constant activation rate. This is observed after insertion and before closing. Before the soft tissue or skin is sutured, alveolar distraction osteogenesis device 69 is activated until the soft tissue begins to blanch. Blanch occurs when the blood circulation in the soft tissue becomes impaired. As a result, the soft tissue turns white. This maximum torque setting is then used to maintain a maximum pressure between the bone segments. The pressure is monitored throughout the day and additional torque is applied in order to maintain a maximum pressure. This maximum pressure on the upper alveolus 88 and lower alveolus 89 requires the shortest activation period possible. Using conventional activation rates allows for the pressure to decrease from a maximum range. Throughout the distraction process of the present invention, this relatively constant maximum pressure is maintained and thus enables optimized bone growth.

In an alternate embodiment, constant activation rates such as distracting bone segments approximately 0.5 mm to approximately 2.00 mm per day are used if optimal bone growth is not required. For example, distraction of small alveolar bone segments generally do not require growing large amounts of bone and a constant activation rate is preferable.

Cannula 31 and adapter 32 then may be removed, as will be described below and illustrated in FIG. 6.

Figure 6:
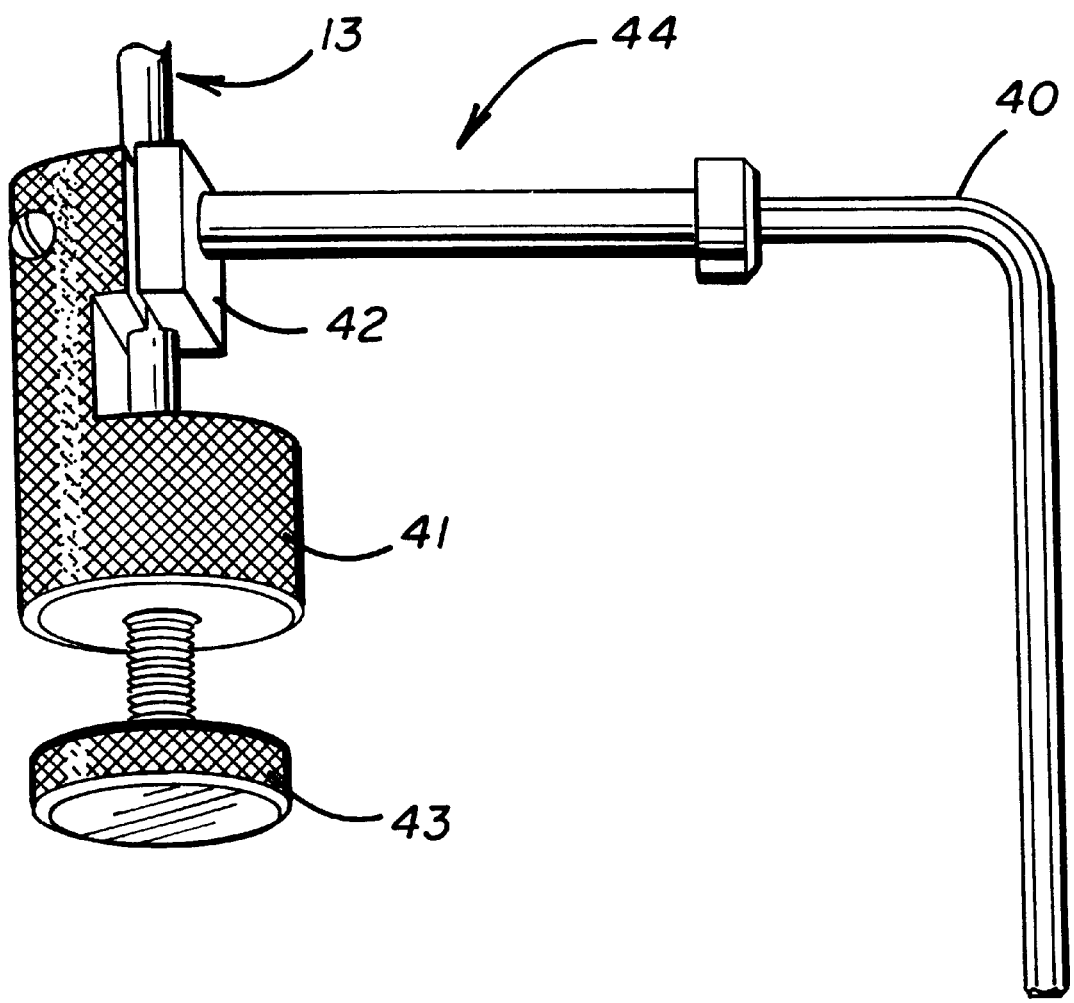
FIG. 6 illustrates a cannula removal device according to the present invention.

FIG. 6 illustrates a cannula and rod removal device 44, according to the present invention. Cannula and rod removal device 44, along with alien wrench 40, is used to remove a cannula 31 and activation rod 32a after activation. Torque wrench interface adapter 32c, as illustrated in FIG. 1, is removed before using the cannula and rod removal device 44. Torque wrench adapter interface 32c is coupled to activation rod 32a by a set screw which may be loosened to remove adapter interface 32c. Cannula 31 is secured by clamp 42 by rotating allen wrench 40. After the cannula 31 is secured, the cannula can be removed by rotating knob 43 and holding cylindrical portion 41, forcing a piston against activation rod 32a in cannula 31. The cannula 31 and rod 32a are then dislodged and may be removed.

Figure 5B:
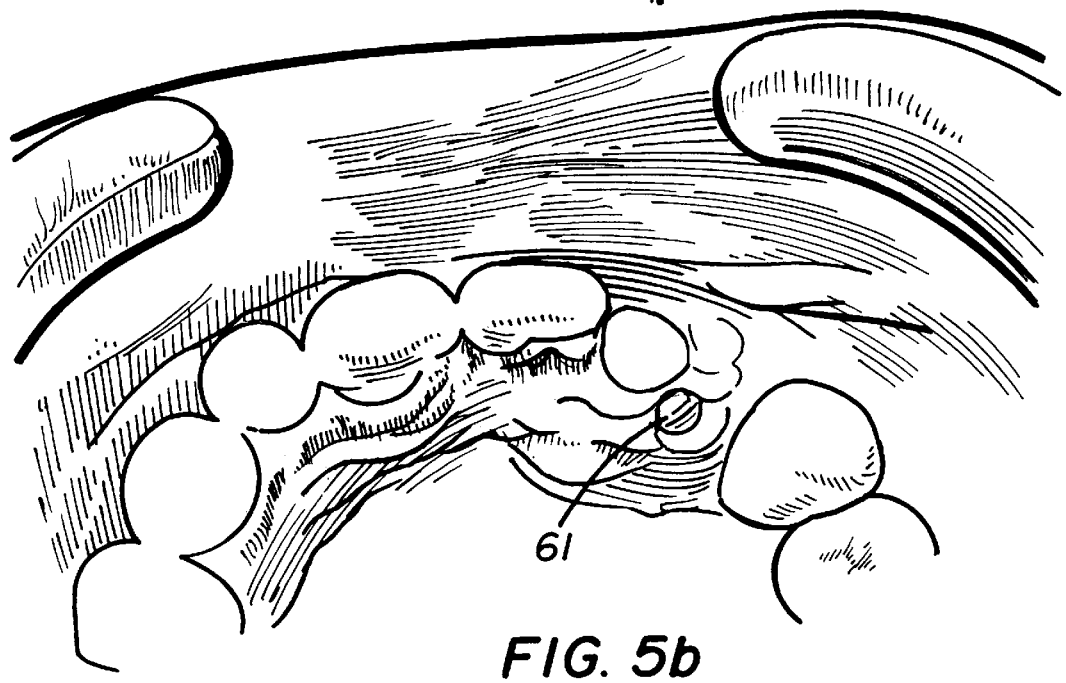
FIG. 5b illustrates an inserted activated alveolar distraction osteogenesis device.

FIG. 5b illustrates a submerged alveolar distraction osteogenesis device in which only base 61 of rod 60 is visible. In an embodiment, base 61 may be used to position a temporary dental prosthesis. Thus, the alveolar distraction device is implanted and has a more cosmetically appealing appearance.

Figure 12A:
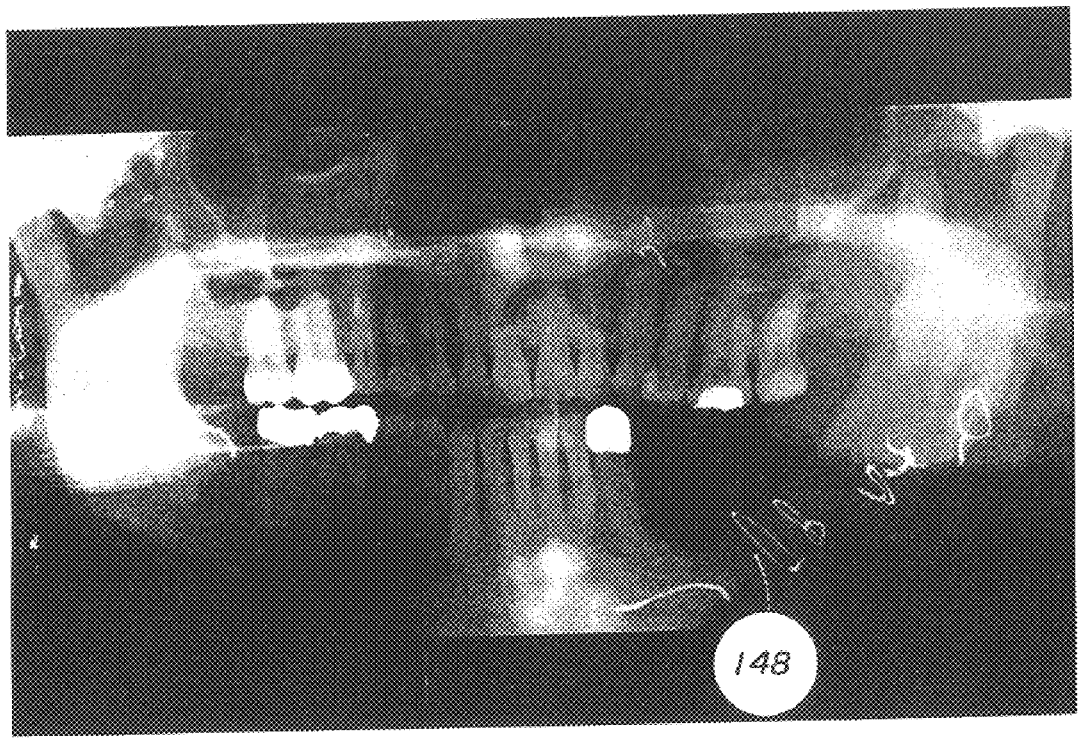
FIG. 12a illustrates a small alveolar bone before insertion of an alveolar distraction device according to another embodiment of the present invention.
Figure 12B:
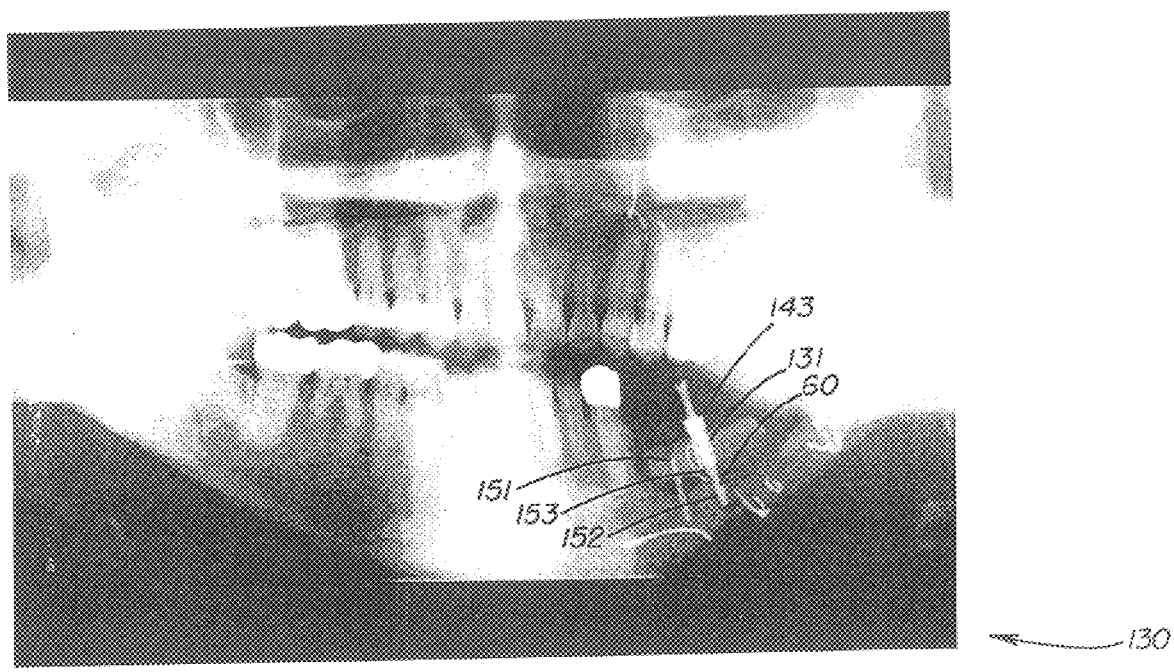
FIG. 12b illustrates the inserted alveolar distraction device in an activated position according to another embodiment of the present invention.
Figure 12C:
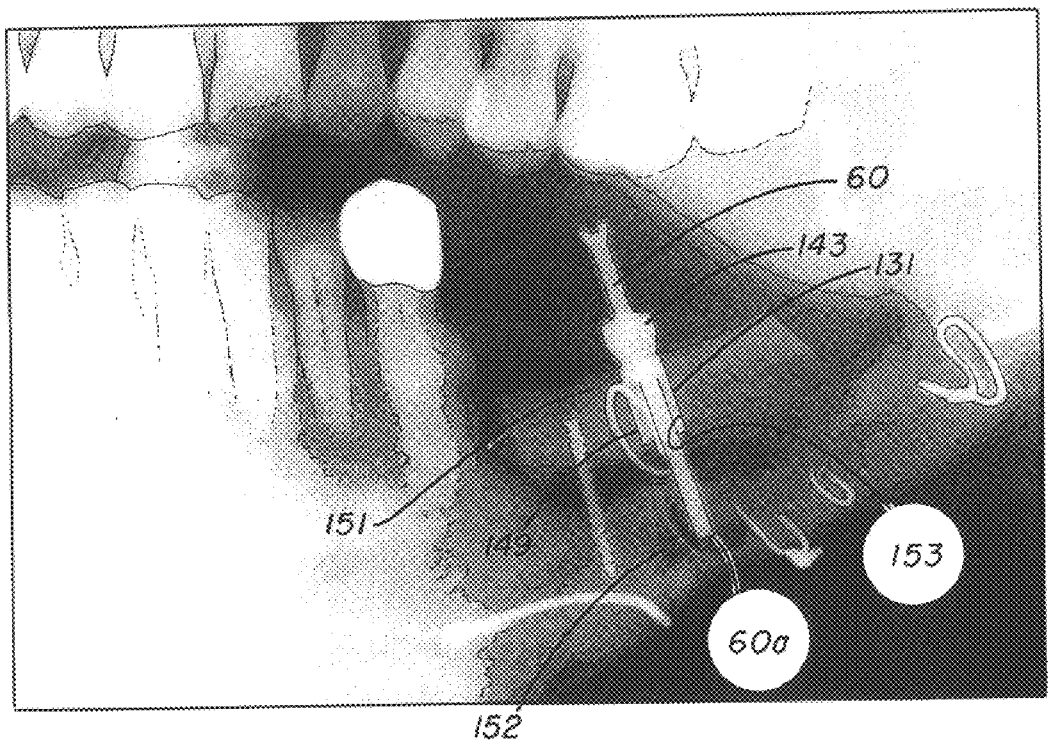
FIG. 12c illustrates an expanded view of the inserted alveolar distraction device in an activated position according to another embodiment of the present invention.
Figure 12D:
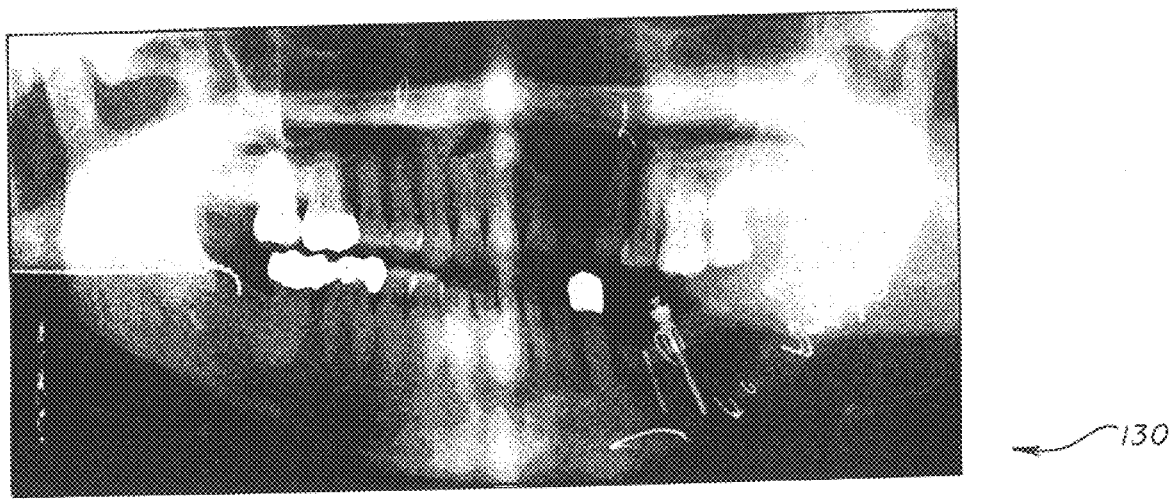
FIG. 12d illustrates the inserted alveolar distraction device after activation according to another embodiment of the present invention.

FIGS. 12a–d illustrate a surgical view of an osteotomy and an inserted alveolus distraction osseointegration device according to another embodiment of the present invention. Specifically, FIG. 12a illustrates an alveolar bone 148 before insertion of the alveolar distraction device 130. In FIGS. 12a–b, an opening 149 is first drilled into the alveolar bone 148. In an embodiment, an approximately 3.3 mm wide opening is formed. The transport cylindrical member 131, covered with a coating 138 of bondable titanium plasma or hydroxlyappatite, is then positioned in the alveolar bone 148. An obturating screw 134 is inserted into the internal opening 132 of the transport cylindrical member 131 to protect the internal threads of the transport cylindrical member 131 from growing bone and tissue while the alveolus bone 148 grows into substantially intimate contact with the transport cylindrical member 131. The transport cylindrical member 131 and screw 134 remains in place for approximately 3 to 5 months while the osseointegration process occurs between the transport cylindrical member 131 and the alveolus bone 148. Once the transport cylindrical member 131 is rigidly bonded to the alveolus bone 148, the obturating screw is removed and a second surgical method is performed. The drill guide 139 is then inserted into the transport cylindrical member 131. A surgical drill is inserted into the opening of the drill guide 139 and a hole 153 is drilled further into the alveolus bone 148. The drill guide 139 protects the internal threads of the transport cylindrical member 131 during drilling of the hole 153 in the alveolus bone 148. The hole 153 is located concentrically with the transport cylindrical member 131. The drill guide 139 is then removed. A drill and saw are then used to perform the osteotomy to mobilize the alveolus bone 148 containing the osseointegrated transport cylindrical member 131 and hole 153. The osteotomy forms a first bone segment 151 and a second bone segment 152 wherein the first bone segment 151 contains the cylindrical member 131 and hole 153. A rod adapter 143 is inserted into the transport cylindrical member 131. The rod adapter 143 has an opening 146 which reduces the internal thread diameter of the transport cylindrical member 131. Rod 60 is then inserted into opening 149 through the alveolus segment and through opening 146 of the rod adapter 143. Rod 60 extends through hole 153 and rod end 60a is then positioned against the second alveolus bone segment 152.

A stabilizing plate 64, as described above in the first embodiment, may or may not be utilized in the second embodiment. The use of a stabilizing plate 64 is dependent upon whether the bone material of the second bone segment 152 is sufficiently hard.

The alveolar distraction device according to the second embodiment may be activated using a hexagonal drive wrench or slot screw driver that mates with the base 61 of rod 60. In an embodiment, base 61 is hexagonally shaped or circular having a slot. The cannula 31, adapter 32 and end 62 are not utilized in activation of the alveolar distraction device according to the second embodiment. Similarly, cannula and rod removal device 44 illustrated in FIG. 6 is not necessary in the second embodiment. As discussed above, a constant activation rate may be used to exert a force between the first alveolus bone segment 151 and the second alveolus bone segment 152 by setting the hexagonal drive wrench to a predetermined setting or using a slot screw driver. The constant activation rate may be from approximately 0.5 mm to approximately 2.0 mm per day, thus ensuring optimal bone growth. In an embodiment, once the distraction process is complete and the rod 60 is fully inserted, the rod 60 remains in the bone for approximately 3 to 5 weeks. The rod 60 is then removed by rotating the base 61 clockwise. A Trephine surgical hole saw is then used to mobilize and remove the cylindrical member 131 and rod adapter 143 or 147 from the alveolar bone. If a stabilizing plate 64 was utilized, it is then removed. A dental implant may then be inserted.

Although two surgical procedures are performed in the alveolar distraction device according to the second embodiment, this device is preferred when distraction of small and thin alveolar bone is required.

The foregoing description of the preferred embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An osteogenesis distraction apparatus for distracting of a first alveolar bone segment from a second alveolar bone segment, comprising:

(a) a cylindrical member having a threaded inner surface for coupling to the first alveolar bone segment;

(b) a rod adapter having a threaded outer surface and a threaded inner surface, the threaded outer surface for mating to the threaded inner surface of the cylindrical member; and (c) a rod having a base and a threaded outer surface for mating to the threaded inner surface of the rod adapter, wherein the rod is for positioning the first alveolar bone segment a distance from the second alveolar bone segment, responsive to a force.

2. The osteogenesis distraction apparatus of claim 1, further comprising an activating means coupled to the base of the rod for transferring a force.

3. The osteogenesis distraction apparatus of claim 2, wherein the rod is removed by rotating the base clockwise.

4. The osteogenesis distraction apparatus of claim 1, further comprising:

an obturating member having a threaded outer surface which mates with the threaded inner surface of the cylindrical member, the obturating member for preventing bone from growing into the cylindrical member while the alveolus grows into substantially intimate contact with the cylindrical member.

5. The osteogenesis distraction apparatus of claim 1, further comprising:

a drill guide member having a threaded outer surface and an inner opening, the threaded outer surface for mating with the threaded inner surface of the cylindrical member, and the inner opening for guiding a drill.

6. The osteogenesis distraction apparatus of claim 1, wherein said cylindrical member is covered with a coating for enhancing an osseointegration process.

7. The osteogenesis distraction apparatus of claim 6, wherein said coating is a bondable titanium plasma.

8. The osteogenesis distraction apparatus of claim 6, wherein said coating is a bondable hydroxlyappatite.

9. A method for forming alveolus, comprising the steps of:

(a) forming an opening in the alveolus;

(b) inserting a cylindrical member into the opening in the alveolus;

(c) inserting an obturating member in the cylindrical member to prevent bone and tissue from growing into the cylindrical member while the alveolus grows into substantially intimate contact with the cylindrical member;

(d) removing the obturating member;

(e) inserting a drill guide member in the cylindrical member;

(f) forming a second opening in the alveolus with a drill guided by the drill guide member;

(g) removing the drill guide member;

(h) cutting the alveolus into a first bone segment and a second bone segment, the first bone segment containing the cylindrical member and the second opening;

(i) inserting a rod adapter into the cylindrical member;

(j) inserting a rod into the opening of the alveolus and through the rod adapter to the second bone segment; and, (k) exerting a force on the rod in order to displace the first bone segment from the second bone segment.

10. The method of claim 9, wherein the alveolus grows into substantially intimate contact with the cylindrical member for approximately 3 to 5 months.

11. The method of claim 9, wherein the rod remains in the alveolus for approximately 3 to 5 weeks after complete activation.

12. A method for forming alveolus, comprising the steps of:

(a) forming an opening in the alveolus;

(b) inserting a cylindrical member into the opening in the alveolus;

(c) forming a second opening in the alveolus with a drill guide inserted into the cylindrical member;

(d) cutting the alveolus into a first bone segment and a second bone segment, the first bone segment containing the cylindrical member;

(e) inserting a rod adapter into the cylindrical member;

(f) inserting a rod into the opening of the alveolus and through the rod adapter to the second bone segment; and, (g) exerting a force on the rod in order to displace the first bone segment from the second bone segment.

* * * * *